United States Patent [19]

Davis et al.

[11] 4,388,358
[45] Jun. 14, 1983

[54] ADAPTIVE SUPPORT SYSTEM

[75] Inventors: Thomas A. Davis, Scotch Plains, N.J.; Donald R. Cowsar, Birmingham, Ala.

[73] Assignees: University of Alabama; Southern Research Institute, both of Birmingham, Ala.

[21] Appl. No.: 296,018

[22] Filed: Aug. 25, 1981

Related U.S. Application Data

[62] Division of Ser. No. 101,511, Dec. 7, 1979, Pat. No. 4,327,046.

[51] Int. Cl.³ .................. B32B 1/06; B32B 3/18; B32B 3/26
[52] U.S. Cl. .................. 428/71; 5/449; 428/76; 428/304.4; 428/317.7; 428/319.7; 428/327
[58] Field of Search .......... 5/449, 450, 481; 521/54; 428/35, 68, 71, 74, 76, 304.4, 317.1, 317.3, 317.7, 317.9, 319.3, 319.7, 323, 327

[56] References Cited

U.S. PATENT DOCUMENTS

| | | | |
|---|---|---|---|
| 2,959,508 | 11/1960 | Graham et al. | 521/54 |
| 3,256,133 | 6/1966 | Wright et al. | 428/76 |
| 3,300,421 | 1/1967 | Merriman et al. | 521/54 |
| 3,304,219 | 2/1967 | Nickerson | 428/304.4 |
| 3,806,566 | 4/1974 | Rubens | 428/304.4 |
| 3,863,758 | 2/1975 | Connelly | 428/74 |
| 4,027,888 | 6/1977 | Wilcox | 297/284 |
| 4,055,866 | 11/1977 | Evans | 5/449 |
| 4,213,213 | 7/1980 | Burnett | 5/450 |

OTHER PUBLICATIONS

Technical Bulletin, Epotuf Epoxy Resin Hardener, Reichhold Chemicals, Inc., Mar. 1974.

*Primary Examiner*—William J. Van Balen
*Attorney, Agent, or Firm*—Pennie & Edmonds

[57] ABSTRACT

A rigid, shaped, mass support system, such as support or seating appliances for disabled or handicapped persons, is provided by charging a flexible container (2) made of elastic polymeric film with a uniform mixture of rigid particles of a mesh size relatively small compared to the size of the system and a curable adhesive polymeric binder material. The charged container (2) and its contents are molded to adapt to or fit the shape of the mass, such as the contour of that portion of the body to be supported, and evacuated to remove volatiles and fix the shape of the contents of the container. The adhesive binder is then cured to solidify the molded contents of the container to form a composite, from which the polymeric film can be stripped away, after which an adhesive paint is applied to seal and protect the surface.

5 Claims, 1 Drawing Figure

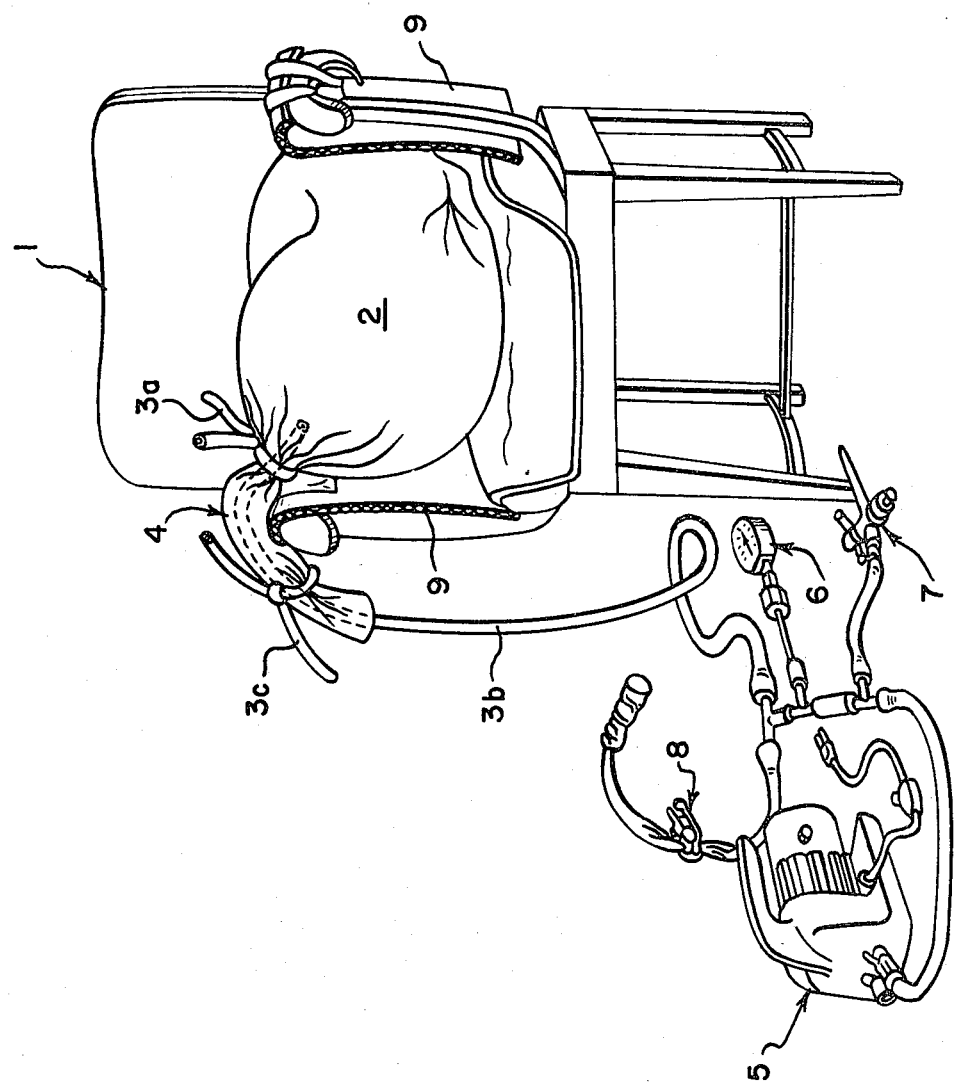

ADAPTIVE SUPPORT SYSTEM

This is a division of application Ser. No. 101,511 filed Dec. 7, 1979, now U.S. Pat. No. 4,327,046.

TECHNICAL FIELD

This invention relates to mass support systems, including support appliances for the human body, e.g., seatings for physically disabled or handicapped patients or persons who, by virtue of their physical condition or other circumstances, are compelled to remain in a given posture over extended periods of time.

More particularly, the invention has to do with a novel adaptive support system, i.e., a support system which is custom-contoured or adapted to the mass or object to be supported, whereby the weight of the latter is uniformly distributed over its interface with the support system.

BACKGROUND ART

Disabled persons of all ages with marked neuromuscular weakness, paralysis, spasticity, bone and other physical deformities, or a combination of these or other maladies and conditions, often are confined to the seated, supine or prone position throughout their daily activities and in many cases are unable to sit or lie down properly. They often lack adequate trunk support and therefore may require a support or seating appliance to counteract tendencies for deformation or further deformation and which will permit them to function and to achieve some degree of comfort.

For example, in the case of wheelchair users, the selection of a suitable appliance in the form of a cushion between the person and the chair is an important factor in determining the degree of the person's independence and mobility since it has a significant impact on the length of time that the user can sit without developing problems such as painful discomfort or even decubitus ulcers (pressure sores). This in turn directly affects the type and extent of the activities, including education and employment, in which the user can partake.

Prior efforts at providing support and seating appliances have often proved inadequate because even with custom-contoured adaptive parts, they failed to meet the particular needs of the individual within reasonable cost. Furthermore, such prior systems have lacked one or more other requirements, including ease of fabrication, low weight (i.e., high strength-to-weight and mass ratio), resistance to soiling, ease of cleaning, non-flammability, temperature stability, and facile utility in the field.

A particularly important consideration in providing adaptive support systems for the physically disabled is the need to maximize the body surface area in contact with the cushion. It is generally agreed that pressure is a cause, not only of induced or aggravated physical deformity, but also of decubitus ulcers. Although the mechanism of decubiti formation is not completely understood, it is believed that pressure contributes to tissue destruction in three ways. First, pressure occludes blood vessels that supply oxygen and nutrients to the skin. Prolonged occlusion can cause ischemia and eventual necrosis. As pressure increases, the time required for tissue destruction is reduced. Second, pressure can cause mechanical destruction of the skin, and tissue that has been damaged by ischemia is more susceptible to such mechanical disruption. The third type of pressure damage, known as "autolysis", occurs when pressure is intermittently applied to tissue, whereupon an inflammatory reaction develops; the repeated application of such pressure causes the cells to release enzymes which catalyze tissue destruction.

Therefore, the incidence of decubiti can be decreased by reducing pressures encountered during sitting. The average pressure (P) is defined as the total force (F) over the total area (A), i.e., $P=F/A$. Since the total force, the body weight being supported, is essentially a constant, a reduction in average pressure is achieved by increasing the area supporting this weight. Furthermore, pressure should be distributed equally over the entire sitting area by equalizing the pressure at all points; this would have the added benefit of minimizing the occurrence of tissue-destructive shear forces parallel to the skin surface.

The foregoing considerations apply also to the more general problem of providing custom-seating for objects or masses which permit the object being supported to be kept in a given stable position for extended periods of time with minimum strain, e.g., splints and orthopedic casts for broken bones, seat cushions for vehicle operators, e.g., truck drivers, and packing molds for transporting delicate objects and equipment.

A need has therefore existed for an adaptive support system which is lightweight and relatively inexpensive to produce on a bespoke basis. In addition to the foregoing objectives, such a system should be capable of being readily formed from kits by technicians, physical therapists and other non-engineering personnel, and once formed should retain its shape with sufficient permanence so as to be re-usable by the subject without the need for re-molding.

Accordingly, it is an object of the present invention to provide an improved mass support system which is custom-contoured to the shape of the mass or object to be supported.

Another object is to provide an improved adaptive support system, such as a support appliance for the physically handicapped or disabled, which can be custom-contoured into a shape which is fixed in relation to the shape of the mass or object to be supported, whereby the weight of the latter is uniformly distributed over its interface with the support system.

Another object is to provide a method of producing an improved mass support system which is custom-contoured to the mass or object to be supported.

Yet another object is to provide a method of forming an improved adaptive support system, such as a support appliance for the physically handicapped or disabled, in which the system is custom-contoured into a shape which is fixed in relation to the shape of the mass or object to be supported, whereby the weight of the latter can be uniformly distributed over its interface with the support system.

These and other objects of the invention as well as a fuller understanding of the advantages thereof can be had by reference to the following disclosure and claims.

DISCLOSURE OF THE INVENTION

The foregoing objects are achieved according to the present invention by a novel, rigid, shaped, mass support system comprising (a) a multiplicity of rigid particles or "beads" of a mesh size relatively small compared to the size of the support system; (b) a cured, rigid, polymeric adhesive binder material uniformly distributed among and bonding the rigid particles; and (c) at least one layer of a coating adhesively applied to the surface of the composite formed by components (a) and (b). The support system is disposable against and substantially rigidly shaped to conform to the shape of the mass so that when the latter is seated on or in the system, the weight of the mass being supported is distributed evenly and uniformly (i.e., without zones or points of substantially greater than average pressure) over the maximum practical interfacial area between the mass and the support system.

The adaptive support system of the present invention possesses a number of advantages over conventional seating devices. For example, in the medical and orthopedic appliance field, the present system can be adapted to furnish support for persons who, for whatever reason, are compelled to remain in a given position or posture for extended periods of time. The system provides a comfortable and beneficial means to achieve this purpose with substantially reduced risk of painful discomfort or development of decubitus ulcers, through the feature in which the weight of the body being supported is evenly and uniformly distributed over the area in which the latter is in contact with the support, regardless of the degree of complexity of its shape.

The support system is produced by the method of the present invention according to which a flexible container made of elastic polymeric film is charged with a uniform mixture comprising the aforesaid rigid particles and curable adhesive resin binder material. Alternatively, the resin is poured into the particle-filled container, and the container and its contents are kneaded to uniformly distribute the resin among the particles. The charged container is then interfaced with the mass or object to be supported and molded, e.g., with hand pressure, to conform it to the shape and contour of the mass or object in a position of function. After the desired shape is obtained, a vacuum is applied to evacuate and devolatilize the contents and rigidify the shape of the container. The subject can be removed and the adhesive resin binder material is then cured to solidify the contents of the molded container to form a rigid shaped composite, from which the polymeric film can be stripped away if desired, in which case a coating which adheres to the shaped composite is applied to seal and protect the surface whereupon the appliance is ready for use.

Particles suitable for use in the present invention should be low in density as well as rigid in order for them to function as a structurally supporting "aggregate" without contributing excessively to the weight of the appliance, whereby the latter will have a desirable high strength-to-weight ratio. For this purpose, rigid polystyrene foam spheres of about 1–5 millimeters average diameter have been found to be particularly suitable, with such spheres having an average diameter of between about 2 and 3 mm being especially preferred.

When polystyrene is used as the particle component, it has been found that the formulation of a satisfactory adhesive binder is difficult because many organic chemicals attack and destroy the integrity of polystyrene foam. Resins which do not adhere well to the beads, such as the RTV silicones, produce crumbly or cheesy structures, and resins which are brittle when cured produce structures which are undesirably hard and friable. Some adhesives cure too fast and others too slowly, the fast-curing resins usually producing excessive amounts of heat. However, it has been found that certain epoxy resins and, alternatively, certain urethane resins are compatible with polystyrene foam. A preferred epoxy-based resin binder material is a two-component system comprising an epoxy resin component such as Epon 828 produced by Shell Oil Company and a hardener component of (i) a fatty amido-amine such as Epotuf 37-620 (Reichhold Chemicals, Inc.), (ii) an amine-terminated butadiene-acrylonitrite copolymer such as Hycar ATBN (B. F. Goodrich Company), and (iii) up to 20–30%, and preferably 25% by weight (based on the weight of (ii)) of a lower alkanol such as methanol or ethanol which can be volatilized in vacuo at ambient temperature. When mixed in the proper proportions, these components provide an adhesive resin binder with a cure rate which affords a "pot life" (i.e., a period of time during which the resin can be molded or worked and evacuated to remove volatiles and fix the shape of container) of about 1 to 2 hours and a room-temperature curing time of about 6 to 8 hours. The proportions of (ii) and (iii) control the flexibility of the binder system and adjust the cure rate. Essentially no heat is generated during the pot life and curing time, which is a desirable feature, particularly in large volume structures in view of the thermoplastic nature of the particle component and in view of the fact that the resin- and particle-filled container is disposed against, while being molded to the shape and contour of, a person's body. The aforesaid epoxy formulation provides a customized support and seating system of exceptional strength, softness and durability.

The long pot life after the epoxy resin binder components are mixed is an advantage in one sense because it gives the fabricator plenty of time to customize the seat before it hardens. However, the long cure time is a disadvantage in certain instances when shorter overall fabrication times are desired, as in the case of applications such as orthopedic casts and splints. Ideally, the resin material would have an infinite pot life, but be curable on demand, when triggered, in a matter of seconds or minutes. As will be described in detail hereinbelow, such a tiggerable or "cure-on-demand" system suitable for use in the present invention has been discovered in the form of polyurethan resins of the Isocure series produced by Ashland Chemical Co. which can be cured in a matter of seconds by exposure to a gaseous tertiary amine catalyst and which are chemically compatible with the preferred polystyrene particles. Other cure-on-demand systems include acid-curable resins such as furfuryl alcohol-peroxide formulations available from Quaker Oats Company which cure instantly upon contact with sulfur dioxide; the peroxide oxidizes the sulfur dioxide to sulfur trioxide which in turn reacts with water in the system to form the sulfuric acid catalyst. Novolak resins based on resorcinol and formaldehyde which are rich in formaldehyde can be cured on demand when gassed with ammonia. Binder resins based on sodium silicate can be so cured by exposure to carbon dioxide.

Flame retardants can be advantageously added to the particulate component and/or to the binder material to fireproof the inner bulk of the adaptive support system. Suitable flame retardants for polystyrene, epoxy resins and polyurethanes include organophosphates and halides, and inorganic phosphates, borates and antimony compounds. These and other useful flame retardants, as well as their mode of application will be apparent to those skilled in the art having the benefit of the present disclosure before them. Non-flammable surface coatings can also be used as will be described in detail hereinbelow.

With respect to the flexible container, commercial "bags" are usually made from flexible vinyl upholstery materials. In attempting to rigidify such conventional bags with the foregoing particle/adhesive resin binder formulation, unexpected problems are encountered. When the adhesive binder is poured into a conventional plastic bag filled with polystyrene beads and the bag is shaped to fit the contours of the patient or object to be supported, the resin can be cured, but the resultant structure has weak spots because the adhesive-coated beads are only loosely packed at best. To ensure tight packing of the beads (so-called "closest packing" being the theoretically preferred limit), it has been discovered that a relatively high vacuum must be applied to evacuate trapped air from the bag and compress it tightly, whereby the beads are held firmly together as the adhesive resin cures. The resulting structure is strong, but since the conventional bag wrinkles badly upon being evacuated, portions of the bag material become imbedded in the surface of the cured particle-adhesive resin composite and cannot be removed without damaging or destroying the surface of the appliance. This problem has been solved according to the invention by using a highly elastic rubber bag for forming the adaptive seating system, preferably a commercial latex rubber weather balloon. When such an elastic container (the inner surface of which can be pre-coated with a suitable mold-release agent) is filled with polystyrene beads and adhesive binder resin, the system has the desirable consistency and feel of bread dough. Because the bag is highly stretchable, it can be molded with hand pressure to virtually any shape and size desired, which is not possible with conventional nonelastic bags. This is a critically important feature, particularly in the case of seating and support appliances for disabled persons, since the surface area of the patient's skin in pressure contact with the system is desirably increased as the subject sinks into the plastic mixture, causing the latter to flow up around the hips and thighs. When the elastic bag is evacuated, it compresses uniformly to produce a seat with a wrinkle-free, smooth surface.

When the present adaptive support system is used for customized supports, the bag can be removed from the rigidified particle/adhesive resin composite structure after the adhesive has hardened, although for some seating applications it may be desirable for the elastic bag to be the functional surface of the finished appliance. When the elastic latex bag is stripped away from the rigidified structure, the surface is usually totally free from gross defects, but it is highly porous and slightly rough. When desired or required, excess material can be cut away, e.g. with an appropriate abrasive or cutting tool, and the contours can be altered somewhat by carefully heating the surface with a hot-air blower such as a hair dryer. Since many disabled patients are incontinent, the surface should be coated with a durable, waterproof film, and preferably one which is non-flammable, non-toxic and non-irritating to skin. Coatings which are suitable for use in the present invention are generally of the class of polymeric latex (aqueous emulsion) paints. These have been found to be chemically inert to the substrate, a desirable feature, and include acrylic and vinyl polymer and vinyl-acrylic and vinyl-vinylidene copolymer aqueous emulsions, of which the "Geon" series (B. F. Goodrich), and particularly Geon 660X1, a vinyl latex, are preferred, not only because of chemical compatibility with the particle/binder system, but because surfaces coated with same are durable and non-flammable, are resistant to ageing, water penetration and staining (e.g., from human body wastes), can be easily cleaned, and are non-toxic and non-irritating to the skin.

The paint can be pigmented or otherwise colored as desired with commercial color concentrates. The coating can be applied by any convenient means, e.g. with a brush, or by spraying or dip-coating, and as many as 12 coats can be applied in this way to produce the desired smooth finish on the surface of the appliance. The first 6 to 8 coats applied to the porous surface will normally soak into the body of the composite structure. Subsequent coats bridge across the particles on the surface to form a continuous smooth film. If desired, thickening agents such as fumed-silica fillers can be incorporated into the paint formulation to increase its bulk viscosity so that one or two coats will be sufficient to produce a smooth finish on the seat. Alternatively, an adhesive primer (e.g., acrylic-type caulks and sealants) can be applied to the uncoated surface beforehand to reduce its porosity, in which case one or two applications of the paint will be sufficient to produce a smooth coating on the seat.

It is a feature of the present support system that the adhesive resin binder/particle composite, although lightweight, is strong enough to be fitted with means for anchoring belts or straps made of webbing or other material in order to fasten the appliance to another structure (e.g., a wheelchair) and/or to secure or restrain the person or object being supported. Such anchoring means can take the form of channels or slots cut into the composite material through which the belt or strap can be inserted, or the ends of the latter can be anchored by means of rivets and/or an appropriate adhesive.

BRIEF DESCRIPTION OF THE DRAWING

Further details of the present invention and its preferred embodiments can be had by reference to the accompanying drawing, which is a perspective view of an embodiment of the components of the adaptive mass support system together with equipment used in carrying out the present method for forming same.

BEST MODE FOR CARRYING OUT THE INVENTION

Referring to the drawing which depicts the present mass support system and equipment used in the method for adapting same for seating a physically disabled person in an upright position, chair 1 is selected after determining the seating needs of the patient. In particular, chair 1 should be slightly larger than would normally fit the individual; the bulk of the finished adaptive support system will set the person up and forward in the chair and can be made to take up the excess space on both sides of the patient's body.

A flexible, elastic polymeric film-like container 2 in the form of a meteorological balloon obtained from the Kaysan Corporation is placed in chair 1 and charged with rigid polystyrene foam particles (2–3 mm average diameter). The amount of particles required for a particular application is determined by pushing the particle-filled container 2 into the approximate shape sought and then adding or removing beads as required. Next, a quantity of the aforementioned adhesive resin binder material sufficient to fill the interstices between the rigid particles is charged to container 2, which is then closed with ¼-inch diameter tubing 3a and kneaded until the resin binder is mixed uniformly with the particles. Uniformity of admixture is achieved when there are no longer any loose particles or lumps of resin and the consistency of the bag resembles that of bread dough.

The container is opened and a length (8–12 feet) of ⅜-inch diameter vacuum tubing 3b is inserted into neck 4 of container 2 until the end of the tubing extends approximately 2 inches into the container cavity. Container 2 is then airtightly sealed to tubing 3b with tubing 3a and ¼-inch diameter tubing 3c and is disposed in chair 1 with the tubing 3b extending away from the side of the bag and with cardboard or other non-abrasive sheet 9 of material inserted between the bag and any open or rough areas on the chair. For instance, if a wheelchair is to be used, the open areas below the armrests on each side of the seat should be so lined to prevent the bag from bulging out through the open areas during molding. Container 2 and its contents are now ready for molding.

With container 2 properly positioned in chair 1, the excess air in the bag is removed through tubing 3b which is connected to a DeVilbiss Company (Somerset, Pa.) Type 561 Air Compressor 5 equipped with pressure gage 6, and stopcocks 7 and 8. After forming a preliminary impression in container 2 (taking into account the seating needs of the patient), the person is placed into the mold and postured in a comfortable and clinically suitable position. When the desired support has been attained, the vacuum is re-applied at 2 inches Hg absolute to fix the shape of the appliance so that the subject can be removed. The vacuum is maintained for 5 hours following completion of the molding process while the resin "sets up". In this connection, it has been found that, because the vacuum maintains the shape of the mold while the resin is "setting up", if the vacuum is excessive, the impression in the mold may shrink, while a vacuum which slackens may cause loss of the impression. For these reasons, it has been found that a vacuum of between 1 and 4 inches Hg absolute is desirable, with 2–3 inches Hg absolute being preferred.

In the particular case of a cure-on-demand resin binder, 5 grams each of Isocure 308 (a polyol) and Isocure 606 (a polyisocyanate) are mixed and added to 400 ml of polystyrene beads (having an average diameter of between 2 and 3 mm) in a flexible, elastic, latex rubber container. The bag and its contents are kneaded until the polyurethane resin components are uniformly distributed among the beads, and then molded into the desired shape and fixed in that position by evacuation in the manner aforesaid. Curing of the resin is initiated by injecting 0.2 ml of triethylamine into the evacuated container; curing is completed by the time all of the amine has been vaporized (about 30 seconds).

In the case of an epoxy resin binder, 47 milliliters of Epotuf 37-620 hardener (a fatty amido-amine produced by Reichhold Chemicals, Inc.) are added to a stirred mixture of 200 grams of Hycar ATBN and 50 milliliters of methanol in a beaker. A quantity (98 grams) of Epon 828 epoxy resin is added and the resulting binder formulation is mixed thoroughly with an electric stirrer and then poured into the balloon containing the polystyrene particles. The balloon is kneaded to ensure thorough mixing and coating of the particles with resin whereupon the system is ready to be molded.

At the end of the curing or setting-up period, the vacuum is released and tubing 3b is removed from container 2. At this point, the rubber covering or sheath can be peeled away from the contents of the container whereupon the surface of the latter can be brushed free of loose particles and then painted and fitted with safety straps after making final adjustments in the fit by trimming away rough or protruding areas with a knife, sandpaper or other abrasive or by heating, e.g., with a hot air gun, and pressing or otherwise smoothening the protruding areas.

The foregoing description and examples are presented for the purpose of illustrating the invention and its advantages without intending to limit same in any way to specific features or embodiments. It is understood that changes and variations can be made in the support system and method of the invention without departing from the scope thereof as defined in the following claims.

Having thus described our invention, what we claim as new and desire to secure by Letters Patent is:

1. A rigid, shaped, mass support system, comprising:
   (a) a multiplicity of rigid particles of polystyrene foam spheres having an average diameter of between about 1 and 5 millimeters.
   (b) a cured, polymeric adhesive binder material uniformly distributed among and bonding the rigid particles to form a rigid composite, said binder material being alternatively selected from the group consisting of (1) a polyurethane formed by curing a mixture of a polyol and a polyisocyanate with a gaseous tertiary amine catalyst, and (2) an epoxy resin cured with a hardener composed of (i) a fatty amido-amine, (ii) an amine-terminated butadiene-acrylonitrile copolymer, and (iii) a lower alkanol; and
   (c) a coating adherent to the surface of the composite and formed of a plurality of coats of polymeric latex paint, said system being disposable against and conforming to the shape of the mass such as the contour of that portion of a person's body which the system is intended to support.

2. A support system according to claim 1 wherein:
   the rigid particles each has an average diameter of between about 2 and 3 millimeters; and
   the polymeric latex paint is a vinyl-vinylidene copolymer latex paint.

3. A rigid, shaped, mass support system, comprising a flexible container made of elastic polymeric film containing:
   (a) a multiplicity of rigid particles of polystyrene foam spheres having an average diameter of between about 1 and 5 millimeters; and
   (b) a cured, polymeric adhesive binder material uniformly distributed among and bonding the rigid particles to form a rigid composite, said binder material comprisng a polyurethane resin which has been cured with a gaseous tertiary amine,
said system being disposable against and conforming to the shape of the mass such as the contour of that portion of a person's body which the system is intended to support.

4. A support system according to claim 3 wherein the rigid particles each has an average diameter of between about 2 and 3 millimeters.

5. A support system according to claim 4 wherein the polymeric film of the container is made of latex rubber.

* * * * *

UNITED STATES PATENT AND TRADEMARK OFFICE
CERTIFICATE OF CORRECTION

PATENT NO. : 4,388,358
DATED : June 14, 1983
INVENTOR(S) : Thomas A. Davis and Donald R. Cowsar It is certified that error appears in the above-identified patent and that said Letters Patent is hereby corrected as shown below:

Colum 4, line 43, "polyurethan" should be --polyurethane--.

Colum 6, line 52, "chain" should be --chair--.

Signed and Sealed this

Sixth Day of December 1983

[SEAL]

Attest:

Attesting Officer

GERALD J. MOSSINGHOFF

Commissioner of Patents and Trademarks